(12) United States Patent
Dittgen et al.

(10) Patent No.: US 8,614,168 B2
(45) Date of Patent: Dec. 24, 2013

(54) USE OF AZOLES FOR INCREASING THE ABIOTIC STRESS RESISTANCE OF PLANTS OR PLANT PARTS

(75) Inventors: Jan Dittgen, Frankfurt (DE); Isolde Häuser-Hahn, Leverkusen (DE); Heinz Kehne, Hofheim (DE); Stefan Lehr, Liederbach (DE); Jörg Tiebes, Frankfurt (DE); Marco Busch, Burscheid-Ösinghausen (DE)

(73) Assignee: Monheim (DE)

( * ) Notice: Subject to any disclaimer, the term of this patent is extended or adjusted under 35 U.S.C. 154(b) by 148 days.

(21) Appl. No.: 13/056,986

(22) PCT Filed: Jul. 24, 2009

(86) PCT No.: PCT/EP2009/005376
§ 371 (c)(1),
(2), (4) Date: Mar. 18, 2011

(87) PCT Pub. No.: WO2010/015337
PCT Pub. Date: Feb. 11, 2010

(65) Prior Publication Data
US 2011/0195841 A1    Aug. 11, 2011

(30) Foreign Application Priority Data

Aug. 2, 2008  (EP) ................................. 08013890

(51) Int. Cl.
| | | |
|---|---|---|
| *A01N 43/653* | (2006.01) | |
| *A01N 37/00* | (2006.01) | |
| *A01N 43/647* | (2006.01) | |
| *A61K 31/33* | (2006.01) | |
| *A61K 31/41* | (2006.01) | |
| *C07C 63/64* | (2006.01) | |
| *C07C 53/134* | (2006.01) | |
| *C07C 57/30* | (2006.01) | |
| *C07D 59/86* | (2006.01) | |
| *C07D 62/38* | (2006.01) | |
| *C07D 65/30* | (2006.01) | |
| *C07D 249/08* | (2006.01) | |
| *C07D 517/00* | (2006.01) | |

(52) U.S. Cl.
USPC .......... 504/272; 504/118; 504/139; 504/142; 504/209; 504/261; 514/183; 514/359; 514/360; 514/383; 548/100; 548/262.2; 548/267.8; 562/459; 562/478; 562/495; 562/496

(58) Field of Classification Search
USPC ................ 504/272, 118, 139, 142, 209, 261; 514/183, 359, 360, 383; 548/100, 548/262.2, 267.8; 562/459, 478, 495, 496
See application file for complete search history.

(56) References Cited

U.S. PATENT DOCUMENTS

| | | | |
|---|---|---|---|
| 7,041,624 B2 * | 5/2006 | Kober et al. .................. | 504/130 |
| 2004/0102322 A1 | 5/2004 | Kober et al. | |
| 2009/0048319 A1 | 2/2009 | Kohle et al. | |
| 2010/0093715 A1 * | 4/2010 | Voeste et al. ............... | 514/229.2 |
| 2010/0317515 A1 * | 12/2010 | Dietz et al. .................... | 504/100 |

FOREIGN PATENT DOCUMENTS

| | | |
|---|---|---|
| CA | 2119806 | 9/1995 |
| EP | 0348767 | 1/1990 |
| GB | 2313595 | 12/1997 |
| JP | 2003325063 | 11/2003 |
| WO | 02083732 | 10/2002 |
| WO | 2007008580 | 1/2007 |
| WO | 2007093535 | 8/2007 |

OTHER PUBLICATIONS

Y-X Wu et al.: "Impact of fungicides on active oxygen species and antioxidant enzymes in spring barley (*Hordeum vulgare* L.) exposed to ozone", Environmental Pollution, 116 (2002) pp. 37-47, XP002437764; ISSN 0269-7491.

M.J. Morrison & C.J. Andrews: "Variable increases in cold hardiness induced in winter rape by plant growth regulatros", J. Plant Growth Regulation (1992) 11 pp. 113-117, XP002562961.

Database WPI Week 200403, Thomson Scientific, London, GB: AN 2004-027378, XP002562962.

Kitahata et al.: "Chemical regulation of abscisic acid catabolism in plants by cytochrome P450 inhibitors", Biooganic & Medicinal Chemistry, Elsevier Science, Oxfor, GB, vol. 13, No. 14, Jul. 15, 2005, pp. 4491-4498, XP004928364, ISSN 0968-0896.

International Search Report of PCT/EP2009/005376 dated Jan. 21, 2010 (9 pages).

International Preliminary Examination Report of PCT/EP2009/005376 dated Jan. 7, 2010 (6 pages) in German.

* cited by examiner

*Primary Examiner* — Jane C Oswecki
(74) *Attorney, Agent, or Firm* — Miles & Stockbridge P.C.

(57) ABSTRACT

The invention relates to the use of at least one compound, selected from the group consisting of tebuconazole, epoxiconazole, metconazole, cyproconazole, prothioconazole and any mixtures thereof, for increasing the resistance of plants to abiotic stress factors.

19 Claims, No Drawings

USE OF AZOLES FOR INCREASING THE ABIOTIC STRESS RESISTANCE OF PLANTS OR PLANT PARTS

CROSS REFERENCE TO RELATED APPLICATIONS

This application is a §371 National Stage Application of PCT/EP2009/005376 filed Jul. 24, 2009, which claims priority to European Application 08013890.2 filed Aug. 2, 2008.

BACKGROUND OF THE INVENTION

1. Field of the Invention

The invention relates to the use of particular azole compounds for enhancing the resistance of plants to abiotic stress factors. The present invention further provides a spray solution which comprises particular azole compounds and can be used for enhancing the resistance of plants to abiotic stress factors. The present invention finally also relates to a method for treatment of plants or plant parts for enhancing resistance to abiotic stress factors.

2. Description of Related Art

A fundamental distinction among possible causes of damage to plants is between biotic and abiotic causes. Most of the biotic causes of damage to plants are known pathogens, which can be controlled by chemical crop protection measures and by resistance breeding. In contrast, abiotic stress is the effect of individual or combined environmental factors (in particular frost, cold, heat and drought) on the metabolism of the plant, which constitutes an unusual stress for the organism. In this context, tolerance to abiotic stress means that plants are capable of enduring the stress situation with substantial retention of performance or with less damage than is observed with corresponding, more stress-sensitive controls.

The effect of moderate stresses over prolonged periods of time or short-term extreme stress may lead to irreversible damage, up to and including the death of the plants. Abiotic stress factors are thus responsible to a considerable degree for harvest losses, or lead to average harvests that are often distinctly below the maximum possible yield (Bray et al.: "Responses to Abiotic Stresses", in: Buchanan, Gruissem, Jones (eds.) "Biochemistry and Molecular Biology of Plants", pages 1158 to 1203, American Society of Plant Physiologists, 2000).

It is known that chemical substances may increase the tolerance of plants to abiotic stress. Such effects, which are frequently also associated with increased yields, are also observed inter alia when particular fungicides are used and have been demonstrated for the group of the strobilurins (Bartlett et al., 2002, Pest Manag Sci 60: 309).

For some azole compounds too, a stress resistance-promoting effect has already been demonstrated. However, this has to date been restricted to azoles of a particular structure type (for example methylazoles); to azoles in combination with abscisic acid (ABA); to azoles causing a significant depression of growth in the treated plants; to applications of the azoles in the treatment of seed or seedlings and to the reduction of damage caused by artificial ozone treatment (see, for example, WO 2007/008580 A; Imperial Chemical Industries PLC, 1985, Research Disclosure 259: 578-582; CA 211 98 06; JP 2003/325063 A; Wu and von Tiedemann, 2002, Environmental Pollution 116: 37-47).

In addition, effects of growth regulators on the stress tolerance of crop plants have been described, including paclobutrazole, a methylazole used as a growth regulator (Morrison and Andrews, 1992, J Plant Growth Regul 11: 113-117; Imperial Chemical Industries PLC, 1985, Research Disclosure 259: 578-582).

The effect of abscisic acid (ABA) as a phytohormone has been described in a large number of physiological processes. For example, ABA acts as a "stress hormone", the formation of which is induced inter alia by drought stress and, inter alia, mediates inhibition of stomatary transpiration (closure of the stomata) (Schopfer, Brennicke: "Pflanzenphysiologie" [Plant Physiology], 5th edition, Springer, 1999). This makes the plant more tolerant to drought stress.

It has been shown in numerous examples that exogenous application of abscisic acid can reduce the sensitivity of plants to stress, or increase stress tolerance (Jones and Mansfield, 1970, J. Exp. Botany 21: 714-719; Bonham-Smith et al., 1988, Physiologia Plantarum 73: 27-30). Furthermore, it was also shown that ABA-analogous structures are capable of triggering ABA-like plant reactions (Churchill et al., 1998, Plant Growth Regul 25: 35-45; Huang et al., 2007, Plant J 50: 414-428). The stress tolerance-enhancing action of ABA analogs in combination with growth inhibitors has likewise already been described (DE 38 215 20 A).

The fungicidal action of azoles such as tebuconazole and prothioconazole is known and is based on the inhibition of sterol C14-demethylase, a central enzyme in sterol biosynthesis (Kuck & Vors: "Sterol Biosynthesis Inhibitors", in: Krämer & Schirmer (eds.) "Modern Crop Protection Compounds", Vol. 2, pages 605 to 650, Wiley-VCH, 2007).

In addition to sterol C14-demethylase, however, other enzymes of the same type (known as P450 monooxygenases) are also inhibited by representatives of these substance classes. For example, many of these molecules also lead, as a result of inhibition of ent-kaurene oxidase after application, to significant stunting of the plants, since the biosynthesis of gibberellic acid is thus inhibited, a plant hormone involved, inter alia, in the regulation of growth processes (Buchenauer: "DMI-fungicides—side effects on the plant and problems of resistance, in: Lyr (ed.) "Modern Selective Fungicides", 2nd ed., p. 259-290, Gustav Fischer Verlag, 1995).

Some representatives of these substance classes have additionally also been described as inhibitors of abscisic acid catabolism (specifically of ABA hydroxylation by ABA 8'-hydroxylase) (Kitahata et al., 2005, Bioorg. Med. Chem. 13: 4491-4498; Saito et al., 2006, Biosci. Biotechnol. Biochem. 70: 1731-1739; Zhang et al., 2007, Journal of Plant Physiology 164: 709-717). The substances described therein, diniconazole and uniconazole, lead, however, to an undesired degree of stunting in some crop plants, for example oilseed rape. The use of these and some other azoles in combination with abscisic acid to increase plant resistance to abiotic stress is described in WO2007/008580 A.

JP 2003-325063 discloses the use of some azoles for treatment of seedlings, which are planted in the soil by means of a machine. The findings described therein are not applicable to a treatment of plants or plant parts to increase resistance to abiotic stress, since the substances act on different plant structures, organs and tissue in seeds and seedlings (for example, cotyledons are physiologically and morphologically different leaves) and are also absorbed via different routes (seed kernel or seedling tissue as opposed to wax layer and leaf tissue of a further-developed plant).

SUMMARY OF THE INVENTION

Proceeding from this prior art, it is an object of the present invention to discover further active ingredients which bring about an enhancement in resistance of the plant to abiotic stress factors and preferably do not lead to any stunting of the crop plants or lead to a significantly lower level thereof than, for example, diniconazole and uniconazole.

For this purpose, several azole compounds for which no effects of this kind have been described to date were tested for their stress resistance-promoting effect on crop plants after spray application.

This found a hitherto unknown positive effect of tebuconazole and prothioconazole on the stress tolerance of crop plants.

This is surprising for tebuconazole, since tebuconazole in studies to date was in clear contrast to uniconazole and diniconazole in having, according to the test system, only slight inhibiting action, if any, on abscisic acid catabolism or ABA 8'-hydroxylase (Kitahata et al., 2005, Bioorg. Med. Chem. 13: 4491-4498; Saito et al., 2006, Biosci. Biotechnol. Biochem. 70: 1731-1739). A corresponding stress tolerance-promoting effect was thus not to be expected on the basis of the prior art for tebuconazole. The findings therefore lead to the conclusion that the corresponding effect does not arise via the inhibition of abscisic acid catabolism or of ABA 8'-hydroxylase, but via another mechanism of action.

For prothioconazole, the stress tolerance-promoting effect is surprising since this compound is an azole thione, and thus differs significantly in structural terms from the compounds described to date for increasing resistance to abiotic stress. Both compounds additionally lead to much lower degrees of stunting in crop plants than, for example, uniconazole or diniconazole.

The stress tolerance-promoting effect of tebuconazole and prothioconazole is thus also significantly greater than would be expected given a linear correlation of growth-regulatory action or stunting and stress tolerance. These findings thus also lead to the conclusion that the corresponding effect of tebuconazole and prothioconazole is imparted only to a minor to insignificant degree via the stunting of the crop plants.

These results obtained for tebuconazole and prothioconazole led to the examination also of the effect of other azoles with respect to enhancement of the resistance of plants to abiotic stress factors in the absence of abscisic acid. At the same time, it was also found for the azoles epoxiconazole, metconazole and cyproconazole that the effect of enhancing the resistance to abiotic stress can also be observed in the absence of abscisic acid.

The present invention accordingly provides for the use of at least one compound selected from the group consisting of tebuconazole, epoxiconazole, metconazole, cyproconazole and prothioconazole, and of any desired mixtures of these azole compounds, for enhancing the resistance of plants to abiotic stress factors, the use of the azoles epoxiconazole and cyproconazole being performed in the absence of abscisic acid.

DETAILED DESCRIPTION OF A PREFERRED EMBODIMENT

In the context of the present invention, the term "resistance to abiotic stress" is understood to mean various benefits for plants which are not directly associated with the known pesticidal activity, preferably fungicidal activity, of the azole compounds. Such advantageous properties are manifested, for example, in the improved plant characteristics specified below: improved root growth with regard to surface area and depth, increased stolon and tiller formation, stronger and more productive stolons and tillers, improvement in shoot growth, increased lodging resistance, increased shoot base diameter, increased leaf area, higher yields of nutrients and constituents, for example carbohydrates, fats, oils, proteins, vitamins, minerals, essential oils, dyes, fibers, better fiber quality, earlier flowering, increased number of flowers, reduced content of toxic products such as mycotoxins, reduced content of residues or disadvantageous constituents of any kind, or better digestibility, improved storage stability of the harvested material, improved tolerance to disadvantageous temperatures, improved tolerance to drought and aridity, and also oxygen deficiency as a result of waterlogging, improved tolerance to elevated salt contents in soil and water, enhanced tolerance to ozone stress, improved compatibility with respect to herbicides and other crop treatment compositions, improved water absorption and photosynthesis performance, advantageous plant properties, for example acceleration of ripening, more homogeneous ripening, greater attractiveness to beneficial animals, improved pollination, or other advantages well known to a person skilled in the art.

The abiotic stress conditions which can be relativized may include, for example, drought, cold and hot conditions, osmotic stress, waterlogging, elevated soil salinity, elevated exposure to minerals, ozone conditions, strong light conditions, limited availability of nitrogen nutrients, limited availability of phosphorus nutrients.

More particularly, the inventive use exhibits the advantages described in spray application to plants and plant parts. Combinations of the azole compounds in question with substances including insecticides, fungicides and bactericides can also be employed in the control of plant diseases in the context of the present invention. In addition, the combined use of azole compounds in question with genetically modified cultivars is also possible, with a view to elevated tolerance to abiotic stress.

In the context of the present invention, a plant is preferably understood to mean a plant from the leaf development stage onward (from stage BBCH 10 according to the BBCH-Monografie der Biologische Bundesanstalt für Land and Forstwirtschaft [BBCH Monograph of the Federal Biological Research Centre for Agriculture and Forestry], 2nd edition, 2001). More particularly, the term "plant" in the context of the present invention does not include seeds and seedlings.

As is well known, some of the various advantages for plants which have been mentioned above can be combined, and documented by generally accepted terms. Such terms are, for example, the following designations: phytotonic effect, resistance to stress factors, less plant stress, plant health, healthy plants, plant fitness, plant wellness, plant concept, vigor effect, stress shield, protective shield, crop health, crop health properties, crop health products, crop health management, crop health therapy, plant health, plant health properties, plant health products, plant health management, plant health therapy, greening effect or regreening effect, freshness, or other terms which are well known to a person skilled in the art.

In the context of the present invention, a good effect on resistance to abiotic stress is understood to mean, without limitation, at least an emergence improved by generally 5%, especially 10%, especially preferably 15%, specifically 20%, at least a yield increased by generally 5%, especially 10%, especially preferably 15%, specifically 20%, at least a root development improved by generally 5%, especially 10%, especially preferably 15%, specifically 20%, at least a shoot size rising by generally 5%, especially 10%, especially preferably 15%, specifically 20%, at least a leaf area increased by generally 5%, especially 10%, especially preferably 15%, specifically 20%, at least an emergence improved by generally 5%, especially 10%, especially preferably 15%, specifically 20%, and/or at least a photosynthetic rate improved by generally 5%, especially 10%, especially preferably 15%, specifically 20%, and the effects may occur individually or else in any combination of two or more effects.

In one embodiment, for example, the azoles provided in accordance with the invention may be applied by spray application to appropriate plants or parts of plants to be treated.

The azoles are used as envisaged in accordance with the invention preferably with a dosage between 0.01 and 3 kg/ha, more preferably between 0.05 and 2 kg/ha, especially preferably between 0.1 and 1 kg/ha.

In addition, it has been found in accordance with the invention that, in the case of the azoles prothioconazole, tebuconazole and metconazole, the inventive action is achieved independently of any abscisic acid added.

In a further embodiment of the present invention, the inventive application of the azoles prothioconazole, tebuconazole and metconazole therefore takes place without the addition of abscisic acid.

In a further embodiment of the present invention, the inventive application of the azoles prothioconazole, tebuconazole and metconazole takes place in the presence of an effective amount of abscisic acid. In this case, a synergistic effect may be found when azoles and abscisic acid are applied at the same time.

If, in the context of the present invention, abscisic acid is used simultaneously with the azoles, for example in the context of a combined preparation or formulation, abscisic acid is preferably added in a dosage between 0.01 and 3 kg/ha, more preferably between 0.05 and 2 kg/ha, especially preferably between 0.1 and 1 kg/ha.

The present invention further provides a spray solution for treatment of plants, comprising an amount, effective for enhancement of the resistance of plants to abiotic stress factors, of at least one compound selected from the group consisting of tebuconazole, epoxiconazole, metconazole, cyproconazole and prothioconazole, and of any desired mixtures of these azole compounds.

The spray solution may comprise other customary constituents, such as solvents, especially water. Further constituents may include active agrochemical ingredients described below.

The content of the at least one azole compound in the spray solution is preferably 0.0005 to 15% by weight, based on the total weight of the spray solution.

In addition to the azoles provided in accordance with the invention, the inventive spray solution preferably also comprises abscisic acid.

If the inventive spray solution comprises abscisic acid, the abscisic acid may be present in an amount of 0.0005 to 15% by weight, based on the total weight of the spray solution.

The present invention further provides for the use of corresponding spray solutions for increasing the resistance of plants to abiotic stress factors.

The remarks which follow apply both to the inventive use of the azole compounds per se and of the corresponding spray solutions.

In accordance with the invention, it has additionally been found that the application, to plants or in their environment, of the azole compounds in combination with at least one fertilizer as defined below is possible.

Fertilizers which can be used in accordance with the invention together with the azole compounds elucidated in detail above are generally organic and inorganic nitrogen-containing compounds, for example ureas, urea/formaldehyde condensation products, amino acids, ammonium salts and ammonium nitrates, potassium salts (preferably chlorides, sulfates, nitrates), salts of phosphoric acid and/or salts of phosphorous acid (preferably potassium salts and ammonium salts). In this context, particular mention should be made of the NPK fertilizers, i.e. fertilizers which contain nitrogen, phosphorus and potassium, calcium ammonium nitrate, i.e. fertilizers which additionally contain calcium, or ammonium nitrate sulfate (general formula $(NH_4)_2SO_4NH_4NO_3$), ammonium phosphate and ammonium sulfate. These fertilizers are generally known to the person skilled in the art; see also, for example, Ullmann's Encyclopedia of Industrial Chemistry, 5th edition, vol. A 10, pages 323 to 431, Verlagsgesellschaft, Weinheim, 1987.

The fertilizers may also contain salts of micronutrients (preferably calcium, sulfur, boron, manganese, magnesium, iron, boron, copper, zinc, molybdenum and cobalt) and phytohormones (for example vitamin B1 and indole-3-acetic acid) or mixtures thereof. Fertilizers used in accordance with the invention may also contain further salts, such as monoammonium phosphate (MAP), diammonium phosphate (DAP), potassium sulfate, potassium chloride, magnesium sulfate. Suitable amounts of the secondary nutrients, or trace elements, are amounts of 0.5 to 5% by weight, based on the overall fertilizer. Further possible ingredients are crop protection compositions, insecticides or fungicides, growth regulators or mixtures thereof. This will be explained in more detail below.

The fertilizers can be used, for example, in the form of powders, granules, prills or compactates. However, the fertilizers can also be used in liquid form, dissolved in an aqueous medium. In this case, it is also possible to use dilute aqueous ammonia as the nitrogen fertilizer. Further possible constituents of fertilizers are described, for example, in Ullmann's Encyclopedia of Industrial Chemistry, 5th edition, 1987, Vol. A 10, pages 363 to 401, DE-A 41 28 828, DE-A 19 05 834 and DE-A 196 31 764.

The general composition of the fertilizers which, in the context of the present invention, may take the form of straight and/or compound fertilizers, for example composed of nitrogen, potassium or phosphorus, may vary within a wide range. In general, a content of 1 to 30% by weight of nitrogen (preferably 5 to 20% by weight), 1 to 20% by weight of potassium (preferably 3 to 15% by weight) and a content of 1 to 20% by weight of phosphorus (preferably 3 to 10% by weight) is advantageous. The microelement content is typically in the ppm range, preferably in the range from 1 to 1000 ppm.

In the context of the present invention, the fertilizer and the azole compound may be administered simultaneously, i.e. synchronously. However, it is also possible first to apply the fertilizer and then the azole compound, or first to apply the azole compound and then the fertilizer. In the case of nonsynchronous application of the azole compound and the fertilizer, the application in the context of the present invention is, however, effected in a functional relationship, especially within a period of generally 24 hours, preferably 18 hours, more preferably 12 hours, specifically 6 hours, more specifically 4 hours, even more specifically within 2 hours. In very particular embodiments of the present invention, the active azole ingredients provided in accordance with the invention and the fertilizer are applied within a time frame of less than 1 hour, preferably less than 30 minutes, more preferably less than 15 minutes.

The active ingredients for use in accordance with the invention, if appropriate in combination with fertilizers, can preferably be employed in the following plants, the enumeration which follows being nonlimiting.

Preferred plants are those from the group of the useful plants, ornamentals, turfs, commonly used trees employed as ornamentals in the public and domestic sectors, and forestry trees. Forestry trees include trees for the production of timber, cellulose, paper and products made from parts of the trees.

The term "useful plants" as used here refers to crop plants which are employed as plants for obtaining foodstuffs, feedstuffs, fuels or for industrial purposes.

The useful plants include, for example, the following types of plants: triticale, durum (hard wheat), turf, vines, cereals, for example wheat, barley, rye, oats, hops, rice, corn and millet/sorghum; beet, for example sugar beet and fodder beet; fruits, for example pome fruit, stone fruit and soft fruit, for example apples, pears, plums, peaches, almonds, cherries and berries, for example strawberries, raspberries, blackberries; legumes, for example beans, lentils, peas and soybeans; oil crops, for example oilseed rape, mustard, poppies, olives, sunflowers, coconuts, castor oil plants, cacao beans and peanuts; cucurbits, for example pumpkin/squash, cucumbers and melons; fiber plants, for example cotton, flax, hemp and jute; citrus fruit, for example, oranges, lemons, grapefruit and tangerines; vegetables, for example spinach, lettuce, asparagus, cabbage species, carrots, onions, tomatoes, potatoes and bell peppers; Lauraceae, for example avocado, *Cinnamomum*, camphor, or also plants such as tobacco, nuts, coffee, aubergine, sugarcane, tea, pepper, grapevines, hops, bananas, latex plants and ornamentals, for example flowers, shrubs, deciduous trees and coniferous trees. This enumeration does not constitute a limitation.

The following plants are considered to be particularly suitable target crops for the application of the inventive method: oats, rye, triticale, durum, cotton, aubergine, turf, pome fruit, stone fruit, soft fruit, corn, wheat, barley, cucumber, tobacco, vines, rice, cereals, pear, pepper, beans, soybeans, oilseed rape, tomato, bell pepper, melons, cabbage, potatoes and apples.

Examples of trees which can be improved in accordance with the inventive method include: *Abies* sp., *Eucalyptus* sp., *Picea* sp., *Pinus* sp., *Aesculus* sp., *Platanus* sp., *Tilia* sp., *Acer* sp., *Tsuga* sp., *Fraxinus* sp., *Sorbus* sp., *Betula* sp., *Crataegus* sp., *Ulmus* sp., *Quercus* sp., *Fagus* sp., *Salix* sp., *Populus* sp.

Preferred trees which can be improved in accordance with the inventive method include: from the tree species *Aesculus: A. hippocastanum, A. pariflora, A. carnea*; from the tree species *Platanus: P. aceriflora, P. occidentalis, P. racemosa*; from the tree species *Picea: P. abies*; from the tree species *Pinus: P. radiate, P. ponderosa, P. contorta, P. sylvestre, P. elliottii, P. montecola, P. albicaulis, P. resinosa, P. palustris, P. taeda, P. flexilis, P. jeffregi, P. baksiana, P. strobes*; from the tree species *Eucalyptus: E. grandis, E. globulus, E. camadentis, E. nitens, E. obliqua, E. regnans, E. pilularus.*

Very particularly preferred trees which can be improved in accordance with the inventive method include: from the tree species *Pinus: P. radiate, P. ponderosa, P. contorta, P. sylvestre, P. strobes*; from the tree species *Eucalyptus: E. grandis, E. globulus* and *E. camadentis.*

Very particularly preferred trees which can be improved in accordance with the inventive method include: horse chestnut, Platanaceae, linden tree, maple tree.

The present invention can also be applied to any turf grasses, including cool-season turf grasses and warm-season turf grasses. Examples of cool-season turf grasses are bluegrasses (*Poa* spp.), such as Kentucky bluegrass (*Poa pratensis* L.), rough bluegrass (*Poa trivialis* L.), Canada bluegrass (*Poa compressa* L.), annual bluegrass (*Poa annua* L.), upland bluegrass (*Poa glaucantha* Gaudin), wood bluegrass (*Poa nemoralis* L.) and bulbous bluegrass (*Poa bulbosa* L.); bentgrasses (*Agrostis* spp.) such as creeping bentgrass (*Agrostis palustris* Huds.), colonial bentgrass (*Agrostis tenuis* Sibth.), velvet bentgrass (*Agrostis canina* L.), South German Mixed Bentgrass (*Agrostis* spp. including *Agrostis tenius* Sibth., *Agrostis canina* L., and *Agrostis palustris* Huds.), and redtop (*Agrostis alba* L.);

fescues (*Festuca* spp.), such as red fescue (*Festuca rubra* L. spp. *rubra*), creeping fescue (*Festuca rubra* L.), chewings fescue (*Festuca rubra commutata* Gaud.), sheep fescue (*Festuca ovina* L.), hard fescue (*Festuca longifolia* Thuill.), hair fescue (*Festucu capillata* Lam.), tall fescue (*Festuca arundinacea* Schreb.) and meadow fescue (*Festuca elanor* L.);

ryegrasses (*Lolium* spp.), such as annual ryegrass (*Lolium multiflorum* Lam.), perennial ryegrass (*Lolium perenne* L.) and italian ryegrass (*Lolium multiflorum* Lam.);

and wheatgrasses (*Agropyron* spp.), such as fairway wheatgrass (*Agropyron cristatum* (L.) Gaertn.), crested wheatgrass (*Agropyron desertorum* (Fisch.) Schult.) and western wheatgrass (*Agropyron smithii* Rydb.).

Examples of further cool-season turfgrasses are beachgrass (*Ammophila breviligulata* Fern.), smooth bromegrass (*Bromus inermis* Leyss.), cattails such as Timothy (*Phleum pratense* L.), sand cattail (*Phleum subulatum* L.), orchardgrass (*Dactylis glomerata* L.), weeping alkaligrass (*Puccinellia distans* (L.) Parl.) and crested dog's-tail (*Cynosurus cristatus* L.).

Examples of warm-season turfgrasses are Bermudagrass (*Cynodon* spp. L. C. Rich), zoysiagrass (*Zoysia* spp. Willd.), St. Augustine grass (*Stenotaphrum secundatum* Walt Kuntze), centipedegrass (*Eremochloa ophiuroides* Munro Hack.), carpetgrass (*Axonopus affinis* Chase), Bahia grass (*Paspalum notatum* Flugge), Kikuyugrass (*Pennisetum clandestinum* Hochst. ex Chiov.), buffalo grass (*Buchloe dactyloids* (Nutt.) Engelm.), Blue gramma (*Bouteloua gracilis* (H.B.K.) Lag. ex Griffiths), seashore *paspalum* (*Paspalum vaginatum* Swartz) and sideoats grama (*Bouteloua curtipendula* (Michx. Torr.). Cool-season turfgrasses are generally preferred for the use in accordance with the invention. Especially preferred are bluegrass, bentgrass and redtop, fescues and ryegrasses. Bentgrass is especially preferred.

Particular preference is given in accordance with the invention to treating plants of the plant cultivars which are in each case commercially available or in use. Plant cultivars are understood to mean plants which have new properties ("traits") and which have been obtained by conventional breeding, by mutagenesis or with the aid of recombinant DNA techniques. Crop plants may accordingly be plants which can be obtained by conventional breeding and optimization methods or by biotechnological and genetic engineering methods or combinations of these methods, including the transgenic plants and including the plant varieties which can and cannot be protected by plant breeders' rights.

The inventive treatment method can thus also be used for the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example antisense technology, cosuppression technology or RNAi technology [RNA interference]). A heterologous gene that is located in the genome is also called a transgene. A transgene that is defined by its particular location in the plant genome is called a transformation or transgenic event.

Plants and plant varieties which are preferably treated according to the invention include all plants which have genetic material which imparts particularly advantageous, useful traits to these plants (whether obtained by breeding and/or biotechnological means).

Plants and plant varieties which may also be treated according to the invention are those plants which are resistant to one or more abiotic stress factors. Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or shade avoidance.

Plants and plant varieties which may also be treated according to the invention are those plants characterized by enhanced yield characteristics. Enhanced yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can also be affected by improved plant architecture (under stress and non-stress conditions), including early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may likewise be treated according to the invention are hybrid plants that already express the characteristics of heterosis, or hybrid vigor, which results in generally higher yield, vigor, health and resistance toward biotic and abiotic stress factors. Such plants are typically made by crossing an inbred male-sterile parent line (the female parent) with another inbred male-fertile parent line (the male parent). Hybrid seed is typically harvested from the male-sterile plants and sold to growers. Male-sterile plants can sometimes (e.g. in corn) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species (WO 1992/005251, WO 1995/009910, WO 1998/27806, WO 2005/002324, WO 2006/021972 and U.S. Pat. No. 6,229,072). However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar (e.g. WO 1991/002069).

Plants or plant varieties (obtained by plant biotechnology methods such as genetic engineering) which may also be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., Science (1983), 221, 370-371), the CP4 gene of the bacterium *Agrobacterium* sp. (Barry et al., Curr. Topics Plant Physiol. (1992), 7, 139-145), the genes encoding a petunia EPSPS (Shah et al., Science (1986), 233, 478-481), a tomato EPSPS (Gasser et al., J. Biol. Chem. (1988), 263, 4280-4289) or an Eleusine EPSPS (WO 2001/66704). It can also be a mutated EPSPS, as described, for example, in EP-A 0837944, WO 2000/066746, WO 2000/066747 or WO 2002/026995. Glyphosate-tolerant plants can also be obtained by expressing a gene that encodes a glyphosate oxidoreductase enzyme as described in U.S. Pat. No. 5,776,760 and U.S. Pat. No. 5,463,175. Glyphosate-tolerant plants can also be obtained by expressing a gene that encodes a glyphosate acetyl transferase enzyme as described, for example, in WO 2002/036782, WO 2003/092360, WO 2005/012515 and WO 2007/024782. Glyphosate-tolerant plants can also be obtained by selecting plants containing naturally occurring mutations of the above-mentioned genes as described, for example, in WO 2001/024615 or WO 2003/013226.

Other herbicide-resistant plants are for example plants which have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species for example). Plants expressing an exogenous phosphinothricin acetyltransferase have been described, for example, in U.S. Pat. No. 5,561,236; U.S. Pat. No. 5,648,477; U.S. Pat. No. 5,646,024; U.S. Pat. No. 5,273,894; U.S. Pat. No. 5,637,489; U.S. Pat. No. 5,276,268; U.S. Pat. No. 5,739,082; U.S. Pat. No. 5,908,810 and U.S. Pat. No. 7,112,665.

Further herbicide-tolerant plants are also plants that have been made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally occurring resistant HPPD enzyme, or a gene encoding a mutated HPPD enzyme according to WO 1996/038567, WO 1999/024585 and WO 1999/024586. Tolerance to HPPD inhibitors can also be obtained by transforming plants with genes encoding certain enzymes enabling the formation of homogentisate despite the inhibition of the native HPPD enzyme by the HPPD inhibitor. Such plants and genes are described in WO 1999/034008 and WO 2002/36787. Tolerance of plants to HPPD inhibitors can also be improved by transforming plants with a gene encoding an enzyme prephenate dehydrogenase in addition to a gene encoding an HPPD-tolerant enzyme, as described in WO 2004/024928.

Further herbicide-resistant plants are plants that have been made tolerant to acetolactate synthase (ALS) inhibitors. Known ALS inhibitors include, for example, sulfonylurea, imidazolinone, triazolopyrimidines, pyrimidinyl oxy(thio) benzoates, and/or sulfonylaminocarbonyltriazolinone herbicides. Different mutations in the ALS enzyme (also known as acetohydroxy acid synthase, AHAS) are known to confer tolerance to different herbicides and groups of herbicides, as described, for example, in Tranel and Wright, Weed Science (2002), 50, 700-712, and also in U.S. Pat. No. 5,605,011, U.S. Pat. No. 5,378,824, U.S. Pat. No. 5,141,870 and U.S. Pat. No. 5,013,659. The production of sulfonylurea-tolerant plants and imidazolinone-tolerant plants has been described in U.S. Pat. No. 5,605,011; U.S. Pat. No. 5,013,659; U.S. Pat. No. 5,141,870; U.S. Pat. No. 5,767,361; U.S. Pat. No. 5,731,180; U.S. Pat. No. 5,304,732; U.S. Pat. No. 4,761,373; U.S. Pat. No. 5,331,107; U.S. Pat. No. 5,928,937; and U.S. Pat. No. 5,378,824; and also in the international publication WO 1996/033270. Further imidazolinone-tolerant plants have also been described, for example in WO 2004/040012, WO 2004/106529, WO 2005/020673, WO 2005/093093, WO 2006/007373, WO 2006/015376, WO 2006/024351 and WO 2006/060634. Further sulfonylurea- and imidazolinone-tolerant plants have also been described, for example in WO 2007/024782.

Other plants tolerant to imidazolinone and/or sulfonylurea can be obtained by induced mutagenesis, by selection in cell cultures in the presence of the herbicide or by mutation breeding, as described, for example, for soybeans in U.S. Pat. No. 5,084,082, for rice in WO 1997/41218, for sugar beet in U.S. Pat. No. 5,773,702 and WO 1999/057965, for lettuce in U.S. Pat. No. 5,198,599 or for sunflower in WO 2001/065922.

Plants or plant varieties (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al., Microbiology and Molecular Biology Reviews (1998), 62, 807-813, updated by Crickmore et al. (2005) in the *Bacillus thuringiensis* toxin nomenclature, online at: http://www.lifesci.sussex.ac.uk/Home/Neil_Crickmore/Bt/), or insecticidal portions thereof, for example proteins of the Cry protein classes Cry1Ab, Cry1Ac, Cry1F, Cry2Ab, Cry3Ae or Cry3Bb or insecticidal portions thereof; or 2) a crystal protein from *Bacillus thuringiensis* or a portion thereof which is insecticidal in the presence of a second crystal protein other than *Bacillus thuringiensis* or a portion thereof, such as the binary toxin made up of the Cy34 and Cy35 crystal proteins (Moellenbeck et al., Nat. Biotechnol. (2001), 19, 668-72; Schnepf et al., Applied Environm. Microb. (2006), 71, 1765-1774); or 3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A.105 protein produced by corn event MON98034 (WO 2007/027777); or 4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/home/Neil_Crickmore/Bt/vip.html, for example proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 1994/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants, by using different proteins insecticidal to the same target insect species but having a different mode of action, such as binding to different receptor binding sites in the insect.

Plants or plant varieties (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:

a. plants which contain a transgene capable of reducing the expression and/or the activity of the poly(ADP-ribose) polymerase (PARP) gene in the plant cells or plants, as described in WO 2000/004173 or EP 04077984.5 or EP 06009836.5.

b. plants which contain a stress tolerance-enhancing transgene capable of reducing the expression and/or the activity of the PARG encoding genes of the plants or plant cells, as described, for example, in WO 2004/090140;

c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyl transferase, nicotinamide adenine dinucleotide synthetase or nicotinamide phosphoribosyltransferase, as described, for example, in EP 04077624.7 or WO 2006/133827 or PCT/EP07/002,433.

Plants or plant varieties (obtained by plant biotechnology methods such as genetic engineering) which may also be treated according to the invention show altered quantity, quality and/or storage stability of the harvested product and/or altered properties of specific ingredients of the harvested product such as, for example:

1) Transgenic plants which synthesize a modified starch which is altered with respect to its chemophysical traits, in particular the amylose content or the amylose/amylopectin ratio, the degree of branching, the average chain length, the distribution of the side chains, the viscosity behavior, the gel resistance, the grain size and/or grain morphology of the starch in comparison to the synthesized starch in wild-type plant cells or plants, such that this modified starch is better suited for certain applications. These transgenic plants synthesizing a modified starch are described, for example, in EP 0571427, WO 1995/004826, EP 0719338, WO 1996/15248, WO 1996/19581, WO 1996/27674, WO 1997/11188, WO 1997/26362, WO 1997/32985, WO 1997/42328, WO 1997/44472, WO 1997/45545, WO 1998/27212, WO 1998/40503, WO 99/58688, WO 1999/58690, WO 1999/58654, WO 2000/008184, WO 2000/008185, WO 2000/28052, WO 2000/77229, WO 2001/12782, WO 2001/12826, WO 2002/101059, WO 2003/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 2000/22140, WO 2006/063862, WO 2006/072603, WO 2002/034923, EP 06090134.5, EP 06090228.5, EP 06090227.7, EP 07090007.1, EP 07090009.7, WO 2001/14569, WO 2002/79410, WO 2003/33540, WO 2004/078983, WO 2001/19975, WO 1995/26407, WO 1996/34968, WO 1998/20145, WO 1999/12950, WO 1999/66050, WO 1999/53072, U.S. Pat. No. 6,734,341, WO 2000/11192, WO 1998/22604, WO 1998/32326, WO 2001/98509, WO 2001/98509, WO 2005/002359, U.S. Pat. No. 5,824,790, U.S. Pat. No. 6,013,861, WO 1994/004693, WO 1994/009144, WO 1994/11520, WO 1995/35026 and WO 1997/20936.

2) Transgenic plants which synthesize non-starch carbohydrate polymers or which synthesize non-starch carbohydrate polymers with altered properties in comparison to wild-type plants without genetic modification. Examples are plants which produce polyfructose, especially of the inulin and levan type, as described in EP 0663956, WO 1996/001904, WO 1996/021023, WO 1998/039460 and WO 1999/024593, plants which produce alpha-1,4-glucans, as described in WO 1995/031553, US 2002/031826, U.S. Pat. No. 6,284,479, U.S. Pat. No. 5,712,107, WO 1997/047806, WO 1997/047807, WO 1997/047808 and WO 2000/14249, plants which produce alpha-1,6-branched alpha-1,4-glucans, as described in WO 2000/73422, and plants which produce alternan, as described in WO 2000/047727, EP 06077301.7, U.S. Pat. No. 5,908,975 and EP 0728213.

3) Transgenic plants which produce hyaluronan, as described, for example, in WO 2006/032538, WO 2007/039314, WO 2007/039315, WO 2007/039316, JP 2006/304779 and WO 2005/012529.

Plants or plant varieties (obtained by plant biotechnology methods such as genetic engineering) which may also be treated according to the invention are plants, such as cotton plants, with altered fiber characteristics. Such plants can be obtained by genetic transformation, or by selection of plants containing a mutation imparting such altered fiber characteristics and include:

a) plants, such as cotton plants, which contain an altered form of cellulose synthase genes, as described in WO 1998/000549;

b) plants, such as cotton plants, which contain an altered form of rsw2 or rsw3 homologous nucleic acids, as described in WO 2004/053219;

c) plants, such as cotton plants, with an increased expression of sucrose phosphate synthase, as described in WO 2001/017333;

d) plants, such as cotton plants, with an increased expression of sucrose synthase, as described in WO 02/45485;

e) plants, such as cotton plants, wherein the timing of the plasmodesmatal gating at the basis of the fiber cell is altered, for example through downregulation of fiber-selective β-1,3-glucanase, as described in WO 2005/017157;

f) plants, such as cotton plants, which have fibers with altered reactivity, for example through the expression of the N-acetylglucosaminetransferase gene including nodC and chitin synthase genes, as described in WO 2006/136351.

Plants or plant cultivars (obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants containing a mutation imparting such altered oil characteristics and include:

a) plants, such as oilseed rape plants, which produce oil having a high oleic acid content, as described, for example, in U.S. Pat. No. 5,969,169, U.S. Pat. No. 5,840,946 or U.S. Pat. No. 6,323,392 or U.S. Pat. No. 6,063,947;

b) plants, such as oilseed rape plants, which produce oil having a low linolenic acid content, as described in U.S. Pat. No. 6,270,828, U.S. Pat. No. 6,169,190 or U.S. Pat. No. 5,965,755;

c) plants, such as oilseed rape plants, which produce oil having a low level of saturated fatty acids, as described, for example, in U.S. Pat. No. 5,434,283.

Particularly useful transgenic plants which may be treated according to the invention are plants which comprise one or more genes which encode one or more toxins and are the transgenic plants available under the following trade names: YIELD GARD® (for example corn, cotton, soybeans), KnockOut® (for example corn), BiteGard® (for example corn), BT-Xtra® (for example corn), StarLink® (for example corn), Bollgard® (cotton), Nucotn® (cotton), Nucotn 33B® (cotton), NatureGard® (for example corn), Protecta® and NewLeaf® (potato). Examples of herbicide-tolerant plants which may be mentioned are corn varieties, cotton varieties and soybean varieties which are available under the following trade names: Roundup Ready® (tolerance to glyphosate, for example corn, cotton, soybeans), Liberty Link® (tolerance to phosphinothricin, for example oilseed rape), IMI® (tolerance to imidazolinone) and SCS® (tolerance to sulfonylurea, for example corn). Herbicide-resistant plants (plants bred in a conventional manner for herbicide tolerance) which may be mentioned include the varieties sold under the name Clearfield® (for example corn).

Particularly useful transgenic plants which may be treated according to the invention are plants containing transformation events, or a combination of transformation events, and that are listed for example in the databases for various national or regional regulatory agencies (see for example http://gmoinfo.jrc.it/gmp_browse.aspx and http://www.agbios.com/dbase.php).

Formulations:

The active azole ingredients to be used in accordance with the invention can be converted to customary formulations, such as solutions, emulsions, wettable powders, water- and oil-based suspensions, powders, dusts, pastes, soluble powders, soluble granules, granules for broadcasting, suspoemulsion concentrates, natural compounds impregnated with active ingredient, synthetic substances impregnated with active ingredient, fertilizers, and also microencapsulations in polymeric substances.

In the context of the present invention, it is especially preferred when the azoles provided in accordance with the invention are used in the form of a spray formulation.

The present invention therefore additionally also relates to a spray formulation for enhancing the resistance of plants to abiotic stress. A spray formulation is described in detail hereinafter:

The formulations for spray application are produced in a known manner, for example by mixing the azoles for use in accordance with the invention with extenders, i.e. liquid solvents and/or solid carriers, optionally with use of surfactants, i.e. emulsifiers and/or dispersants and/or foam formers. Further customary additives, for example customary extenders and solvents or diluents, dyes, wetting agents, dispersants, emulsifiers, antifoams, preservatives, secondary thickeners, stickers, gibberellins and also water, can optionally also be used. The formulations are prepared either in suitable equipment or else before or during application.

The auxiliaries used may be those substances which are suitable for imparting, to the composition itself and/or to preparations derived therefrom (for example spray liquors), particular properties such as particular technical properties and/or else special biological properties. Useful typical auxiliaries include: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethyl sulfoxide).

If the extender used is water, it is also possible to use, for example, organic solvents as auxiliary solvents. Useful liquid solvents are essentially: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulfoxide, and also water.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Useful wetting agents which may be present in the formulations usable in accordance with the invention are all substances which promote wetting and which are conventionally used for the formulation of active agrochemical ingredients. Preference is given to using alkyl naphthalenesulfonates, such as diisopropyl or diisobutyl naphthalenesulfonates.

Useful dispersants and/or emulsifiers which may be present in the formulations usable in accordance with the invention are all nonionic, anionic and cationic dispersants conventionally used for the formulation of active agrochemical ingredients. Usable with preference are nonionic or anionic dispersants or mixtures of nonionic or anionic dispersants. Suitable nonionic dispersants are especially ethylene oxide/propylene oxide block polymers, alkylphenol polyglycol ethers and tristryrylphenol polyglycol ether, and the phosphated or sulfated derivatives thereof. Suitable anionic dispersants are especially lignosulfonates, salts of polyacrylic acid and arylsulfonate/formaldehyde condensates.

Antifoams which may be present in the formulations usable in accordance with the invention are all foam-inhibiting substances conventionally used for the formulation of active agrochemical ingredients. Usable with preference are silicone antifoams and magnesium stearate.

Preservatives which may be present in the formulations usable in accordance with the invention are all substances usable for such purposes in agrochemical compositions. Examples include dichlorophene and benzyl alcohol hemiformal.

Secondary thickeners which may be present in the formulations usable in accordance with the invention are all substances usable for such purposes in agrochemical compositions. Preference is given to cellulose derivatives, acrylic acid derivatives, xanthan, modified clays and finely divided silica.

Stickers which may be present in the formulations usable in accordance with the invention include all customary binders usable in seed-dressing products. Preferred examples include polyvinylpyrrolidone, polyvinyl acetate, polyvinyl alcohol and tylose.

Gibberellins which may be present in the formulations usable in accordance with the invention may preferably be gibberellins A1, A3 (=gibberellic acid), A4 and A7; particular preference is given to using gibberellic acid. The gibberellins are known (cf. R. Wegler "Chemie der Pflanzenschutz- and Schädlingsbekämpfungsmittel" [Chemistry of Crop Protection Compositions and Pesticides], vol. 2, Springer Verlag, 1970, p. 401-412).

Further additives may be fragrances, mineral or vegetable, optionally modified oils, waxes and nutrients (including trace nutrients), such as salts of iron, manganese, boron, copper, cobalt, molybdenum and zinc.

Additionally present may be stabilizers, such as cold stabilizers, antioxidants, light stabilizers or other agents which improve chemical and/or physical stability.

The formulations contain generally between 0.01 and 98% by weight, preferably between 0.5 and 90%, of active azole ingredient.

The inventive active ingredient may be present in its commercially available formulations and in the use forms, prepared from these formulations, in a mixture with other active ingredients, such as insecticides, attractants, sterilants, bactericides, acaricides, nematicides, fungicides, growth regulators, herbicides, safeners, fertilizers or semiochemicals.

In addition, the described positive effect of the azole compounds on the plants' own defenses can be supported by an additional treatment with active insecticidal, fungicidal or bactericidal ingredients.

Preferred times for the application of azole compounds for enhancing resistance to abiotic stress are treatments of the soil, stems and/or leaves with the approved application rates.

The inventive active ingredients may generally additionally be present in their commercial formulations and in the use forms prepared from these formulations in mixtures with other active ingredients, such as insecticides, attractants, sterilants, acaricides, nematicides, fungicides, growth regulators or herbicides.

Particularly favorable mixing partners are, for example, the following compounds:

Fungicides:
inhibitors of nucleic acid synthesis
benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid Inhibitors of Mitosis and Cell Division
benomyl, carbendazim, diethofencarb, fuberidazole, pencycuron, thiabendazole, thiophanat-methyl, zoxamide Inhibitors of Respiratory Chain Complex I/II
diflumetorim
bixafen, boscalid, carboxin, fenfuram, fluopyram, flutolanil, furametpyr, mepronil, oxycarboxin, penthiopyrad, thifluzamide, N-[2-(1,3-dimethylbutyl)phenyl]-5-fluoro-1,3-dimethyl-1H-pyrazole-4-carboxamide Inhibitors of Respiratory Chain Complex III
amisulbrom, azoxystrobin, cyazofamid, dimoxystrobin, enestrobin, famoxadone, fenamidone, fluoxastrobin, kresoxim-methyl, metominostrobin, orysastrobin, pyraclostrobin, pyribencarb, picoxystrobin, trifloxystrobin Decouplers
dinocap, fluazinam Inhibitors of ATP Production
fentin acetate, fentin chloride, fentin hydroxide, silthiofam Inhibitors of Amino Acid Biosynthesis and Protein Biosynthesis
andoprim, blasticidin-S, cyprodinil, kasugamycin, kasugamycin hydrochloride hydrate, mepanipyrim, pyrimethanil Inhibitors of Signal Transduction
fenpiclonil, fludioxonil, quinoxyfen Inhibitors of Lipid and Membrane Synthesis
chlozolinate, iprodione, procymidone, vinclozolin
ampropylfos, potassium-ampropylfos, edifenphos, iprobenfos (IBP), isoprothiolane, pyrazophos
tolclofos-methyl, biphenyl
iodocarb, propamocarb, propamocarb hydrochloride Inhibitors of Ergosterol Biosynthesis
fenhexamid,
azaconazole, bitertanol, bromuconazole, diclobutrazole, difenoconazole, diniconazole, diniconazole-M, etaconazole, fenbuconazole, fluquinconazole, flusilazole, flutriafol, furconazole, furconazole-cis, hexaconazole, imibenconazole, ipconazole, myclobutanil, paclobutrazole, penconazole, propiconazole, simeconazole, spiroxamine, tebuconazole, triadimefon, triadimenol, triticonazole, uniconazole, voriconazole, imazalil, imazalil sulfate, oxpoconazole, fenarimol, flurprimidole, nuarimol, pyrifenox, triforine, pefurazoate, prochloraz, triflumizole, viniconazole,
aldimorph, dodemorph, dodemorph acetate, fenpropimorph, tridemorph, fenpropidin, spiroxamine,
naftifine, pyributicarb, terbinafine Inhibitors of Cell Wall Synthesis
benthiavalicarb, bialaphos, dimethomorph, flumorph, iprovalicarb, polyoxins, polyoxorim, validamycin A Inhibitors of Melanin Biosynthesis
capropamid, diclocymet, fenoxanil, phthalide, pyroquilon, tricyclazole Resistance Induction
acibenzolar-S-methyl, probenazole, tiadinil Multisite
captafol, captan, chlorothalonil, copper salts such as: copper hydroxide, copper naphthenate, copper oxychloride, copper sulfate, copper oxide, oxine-copper and Bordeaux mixture, dichlofluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfur and sulfur preparations containing calcium polysulfide, thiram, tolylfluanid, zineb, ziram Unknown Mechanism
amibromdol, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methyl sulfate, diphenylamine, ethaboxam, ferimzone, flumetover, flusulfamide, fluopicolid, fluoroimid, fosetyl-Al, hexachlorobenzene, 8-hydroxyquinoline sulfate, iprodione, irumamycin, isotianil, methasulfocarb, metrafenone, methyl isothiocyanate, mildiomycin, natamycin, nickel dimethyl dithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden-4-yl)-3-pyridine-carboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3(trifluoromethyl)phenyl]ethylidene]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino]methyl]thio]methyl].alpha.-(methoxymethylene)benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulfonyl)amino]butanamide, 5-chloro-7-(4-methylpiperidin-1-yl)-6-(2,4,6-trifluorophenyl)-[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidin-7-amine, 5-chloro-N-[(1R)-1,2-dimethylpropyl]-6-(2,4,6-trifluorophenyl)[1,2,4]triazolo[1,5-a]pyrimidin-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy)imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3(1-fluoro-2-phenylethyl)oxy]phenyl]ethylidene]amino]oxy]-methyl]-alpha-(methoxyimino)-N-methyl-alphaE-benzacetamide, N-{2-[3-chloro-5-(tri-fluoromethyl)pyridin-2-yl]ethyl}-2-(trifluoromethyl)benzamide, N-(3',4'-dichloro-5-fluoro-biphenyl-2-yl)-3-(difluoromethyl)-1- methyl-1H-pyrazole-4-carboxamide, N-(6-methoxy-3-pyridinyl)cyclopropanecarboxamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide Bactericides:
bronopol, dichlorophen, nitrapyrin, nickel dimethyldithiocarbamate, kasugamycin, octhilinone, furancarboxylic acid, oxytetracycline, probenazole, streptomycin, tecloftalam, copper sulfate and other copper preparations.

Insecticides/Acaricides/Nematicides:
acetylcholine esterase (AChE) inhibitors
carbamates,
for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, fenoxycarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate
organophosphates,
for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulfone, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion Sodium Channel Modulators/Voltage-Dependent Sodium Channel Blockers
pyrethroids,
for example acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, eflusilanate, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans-isomer), prallethrin, profluthrin, protrifenbute, pyresmethrin, resmethrin, RU 15525, silafluofen, tau-fluvalinate, tefluthrin, terallethrin, tetramethrin (1R isomer), tralomethrin, transfluthrin, ZXI 8901, pyrethrins (pyrethrum)

DDT
oxadiazines,
for example indoxacarb
semicarbazone,
for example metaflumizone (BAS3201)

Acetylcholine Receptor Agonists/Antagonists
chloronicotinyls,
for example acetamiprid, AKD 1022, clothianidin, dinotefuran, imidacloprid, imidaclothiz, nitenpyram, nithiazine, thiacloprid, thiamethoxam
nicotines, bensultap, cartap Acetylcholine Receptor Modulators
spinosyns,
for example spinosad,
GABA-controlled chloride channel antagonists
organochlorines,
for example camphechlor, chlordane, endosulfan, gamma-HCH, HCH, heptachlor, lindane, methoxychlor
fiprols,
for example acetoprole, ethiprole, fipronil, pyrafluprole, pyriprole, vaniliprole Chloride Channel Activators
mectins
for example abamectin, emamectin, emamectin-benzoate, ivermectin, lepimectin, milbemycin
juvenile hormone mimetics,
for example diofenolan, epofenonane, fenoxycarb, hydroprene, kinoprene, methoprene, pyriproxifen, triprene Ecdysone Agonists/Disruptors
diacylhydrazines,
for example chromafenozide, halofenozide, methoxyfenozide, tebufenozide Inhibitors of Chitin Biosynthesis
benzoylureas,
for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron
buprofezin
cyromazine Oxidative Phosphorylation Inhibitors, ATP Disruptors
diafenthiuron
organotin compounds,
for example azocyclotin, cyhexatin, fenbutatin-oxide, Oxidative Phosphorylation Decouplers Acting by Interrupting the H-Proton Gradient
pyrroles,
for example chlorfenapyr
dinitrophenols,
for example binapacyrl, dinobuton, dinocap, DNOC, meptyldinocap Side I Electron Transport Inhibitors
METIs,
for example fenazaquin, fenpyroximate, pyrimidifen, pyridaben, tebufenpyrad, tolfenpyrad
hydramethylnon
dicofol Side II Electron Transport Inhibitors
rotenone Side III Electron Transport Inhibitors
acequinocyl, fluacrypyrim Microbial Disruptors of the Insect Gut Membrane
*bacillus thuringiensis* strains Lipid Synthesis Inhibitors
tetronic acids,
for example spirodiclofen, spiromesifen
tetramic acids,
for example spirotetramate, cis-3-(2,5-dimethylphenyl)-4-hydroxy-8-methoxy-1-azaspiro[4.5]dec-3-en-2-one
carboxamides,
for example flonicamid
octopaminergic agonists,
for example amitraz
inhibitors of magnesium-stimulated ATPase
propargite
nereistoxin analogs,
for example thiocyclam hydrogen oxalate, thiosultap-sodium
ryanodin receptor agonists
benzoic acid dicarboxamides,
for example flubendiamide
anthranilamides,
for example Rynaxypyr (3-bromo-N-{4-chloro-2-methyl-6-[(methylamino)carbonyl]phenyl}-1-(3-chloropyridin-2-yl)-1H-pyrazole-5-carboxamide), Cyazypyr (ISO-proposed) (3-bromo-N-{4-cyano-2-methyl-6-[(methylamino)carbonyl]phenyl}-1-(3-chloropyridin-2-yl)-1H-pyrazole-5-carboxamide) (known from WO 2004067528)

Biologicals, Hormones or Pheromones
azadirachtin, *Bacillus* spec., *Beauveria* spec., codlemone, *Metarrhizium* spec., *Paecilomyces* spec., thuringiensin, *Verticillium* spec.

Active Ingredients Having Unknown or Nonspecific Mechanisms of Action
fumigants,
for example aluminum phosphide, methyl bromide, sulfuryl fluoride
antifeedants,
for example cryolite, flonicamid, pymetrozine
mite growth inhibitors,
for example clofentezine, etoxazole, hexythiazox
amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene, verbutin or lepimectin.

The examples which follow describe the invention in detail, but in no way limit the present invention.

Test Description:
Seeds of monocotyledonous and dicotyledonous crop plants are placed in sandy loam in wood-fiber pots, covered with soil and cultivated in a greenhouse under good growth conditions. The test plants are treated in the early leaf stage (BBCH10-BBCH13, BBCH-Monografie der Biologische Bundesanstalt für Land and Forstwirtschaft, 2nd edition, 2001), i.e. 2-3 weeks after sowing according to the species. To ensure uniform water supply before commencement of stress, the potted plants were supplied with the maximum amount of water immediately beforehand by dam irrigation and transferred in plastic inserts in order to prevent subsequent, excessively rapid drying. The inventive compounds, formulated in the form of wettable powders (WP), are then sprayed onto the green parts of the plants as an aqueous suspension at an equivalent water application rate of 600 l/ha with addition of 0.2% wetting agent (agrotin). Substance application is followed immediately by stress treatment of the plants (cold or dry stress).

For cold stress treatment, the plants are kept under the following controlled conditions for 14 days:
"day": 12 hours with illumination at 8° C.
"night": 12 hours without illumination at 1° C.
Dry stress is induced by slow drying under the following conditions:
"day": 14 hours with illumination at 26° C.
"night": 10 hours without illumination at 18° C.

The cold stress phase is ended after exactly 14 days. The duration of the dry stress phase is guided mainly by the state of the untreated, stressed control plants and thus varies from crop to crop. It is ended (by re-irrigating) as soon as irreversible damage is observed on the untreated, stressed control plants. In the case of dicotyledonous crops, for example oilseed rape and soya, the duration of the dry stress phase is between 4 and 6 days, in the case of monocotyledonous crops, for example wheat, barley or corn, between 6 and 10 days.

The end of the stress phase is followed by a 7-day recovery phase, during which the plants are once again kept under good growth conditions in a greenhouse.

In order to rule out any influence of the effects observed by any fungicidal action of the test compounds, it is additionally ensured that the tests proceed without fungal infection and without infection pressure.

After the recovery phase has ended, the intensities of damage are rated visually compared to untreated, unstressed controls of the same age (in the case of dry stress) or the same growth stage (in the case of cold stress). The intensity of damage is first assessed as a percentage (100%=plants have died, 0%=like control plants). These values are then used to calculate the efficacy of the test compounds (=percentage reduction in the intensity of damage as a result of substance application) by the following formula:

$$EF = \frac{(DV_{us} - DV_{ts}) \times 100}{DV_{us}}$$

EF: efficacy (%)
$DV_{us}$: damage value of the untreated, stressed control
$DV_{ts}$: damage value of the plants treated with test compound The table below lists mean values in each case from three results of the same test. The following results were achieved with the inventive compounds under dry stress conditions.

(1) Results of the Individual Substances

| | Test object | | | | | |
|---|---|---|---|---|---|---|
| | BRSNS | | HORVS | | ZEAMX | |
| | | | Stress type | | | |
| Dosage (of each test | dry | | dry | | dry | |
| substance; g/ha) | 250 | 100 | 250 | 100 | 250 | 100 |
| tebuconazole | 42 | 27 | | | 30 | |
| epoxiconazole | | 35 | | 17 | | 11 |
| metconazole | | 50 | | | | |
| cyproconazole | 42 | | | | 37 | 40 |
| prothioconazole | | 12 | | 11 | | 12 |

(2) Results in Combination with ABA

|  | Test object | | | | | | | |
| --- | --- | --- | --- | --- | --- | --- | --- | --- |
|  | BRSNS | | HORVS | | ZEAMX | | ZEAMX | |
|  | | | | Stress type | | | | |
| Dosage (of each test | dry | | dry | | dry | | cold | |
| substance; g/ha) | 250 | 100 | 250 | 100 | 250 | 100 | 250 | 100 |
| tebuconazole + ABA | 65 | 62 | 33 | 22 | 33 | 26 | | |
| metconazole + ABA | | | 44 | 33 | | 23 | | |
| prothioconazole + ABA | 65 | 42 | 33 | 33 | | | 37 | |

Abbreviations:
BRSNS: oilseed rape (*Brassica napus*)
HORVS barley (*Hordeum vulgare*)
ZEAMX: corn (*Zea mais*)

As the results show, inventive compounds have good efficacy against abiotic stress. For example, the inventive compounds at application rates of 0.25 kg or less of active substance per hectare exhibit high efficacy against dry stress, both in monocotyledonous crop plants, for example barley, and in dicotyledonous crop plants, for example oilseed rape.

As the result also show, the stress-reducing action of the inventive compounds can additionally be increased significantly by addition of abscisic acid (ABA).

Stunting:
As already mentioned above, some azoles known from the prior art, which are recommended in combination with abscisic acid to increase plant resistance against abiotic stress (cf. WO2007/008580 A; diniconazole and uniconazole), lead to an undesirable degree of stunting in some crop plants, for example oilseed rape.

In the case of application of the inventive azoles, this stunting occurs to a lower or non-undesirable degree:

| Treatment | Dosage | Mean plant height (cm) |
| --- | --- | --- |
| comparative | | 11.7 |
| uniconazole | 250 g/ha | 6.2 |
| diniconazole | 250 g/ha | 6.7 |
| tebuconazole | 250 g/ha | 10.2 |
| prothioconazole | 250 g/ha | 10.2 |
| epoxiconazole | 250 g/ha | 10.7 |
| metconazole | 250 g/ha | 7.8 |
| cyproconazole | 250 g/ha | 10.8 |

The invention claimed is:

1. A method for synergistically enhancing the resistance of a plant to abiotic stress factors comprising using:
   (1) abscisic acid and
   (2) at least one compound selected from the group consisting of tebuconazole, metconazole, and prothioconazole.

2. The method as claimed in claim 1, wherein the at least one compound is employed in an application rate from 0.01 to 3 kg/ha.

3. The method as claimed in claim 1, wherein the abscisic acid is used in an application rate from 0.01 to 3 kg/ha.

4. The method as claimed in claim 1, wherein the plant is transgenic.

5. The method as claimed in claim 1, further comprising using at least one fertilizer.

6. A synergistic spray solution for treatment of a plant, comprising an amount, effective for enhancement of the resistance of plants to abiotic stress factors, of:
   (1) abscisic acid and
   (2) at least one compound selected from the group consisting of tebuconazole, metconazole, and prothioconazole.

7. The synergistic spray solution as claimed in claim 6, wherein the content of the at least one compound in the spray solution is 0.0005 to 15% by weight, based on the total weight of the spray solution.

8. The synergistic spray solution as claimed in claim 6, wherein the abscisic acid is present in an amount of 0.0005 to 15% by weight, based on the total weight of the spray solution.

9. A method for synergistically enhancing the resistance of a plant to abiotic stress factors comprising using a spray solution as claimed in claim 6.

10. A method for synergistically enhancing the resistance of a plant to abiotic stress factors comprising using a spray solution as claimed in claim 7.

11. A method for synergistically enhancing the resistance of a plant to abiotic stress factors comprising using a spray solution as claimed in claim 8.

12. The method as claimed in claim 1, further comprising using at least an insecticide, fungicide, or bactericide.

13. The method as claimed in claim 1, wherein the at least one compound is employed in an application rate from 0.05 to 2 kg/ha, and the abscisic acid is employed in an application rate from 0.05 to 2 kg/ha.

14. The method as claimed in claim 1, wherein the at least one compound is employed in an application rate from 0.1 to 1 kg/ha, and the abscisic acid is employed in an application rate from 0.1 to 1 kg/ha.

15. The method as claimed in claim 1, wherein the abscisic acid and the at least one compound are applied to soil, a plant, or a plant part.

16. The method as claimed in claim 1, wherein the at least one compound is tebuconazole.

17. The method as claimed in claim 1, wherein the at least one compound is metconazole.

18. The method as claimed in claim 1, wherein the at least one compound is prothioconazole.

19. The method as claimed in claim 1, wherein the plant is corn.

* * * * *